US012151038B2

(12) United States Patent
Krosney et al.

(10) Patent No.: US 12,151,038 B2
(45) Date of Patent: Nov. 26, 2024

(54) INTEGRATED AIR SANITIZER AND SURFACE DISINFECTOR

(71) Applicant: Molekule Group, Inc., Palm Beach Gardens, FL (US)

(72) Inventors: Mark D. Krosney, Jensen Beach, FL (US); Amin J. Khoury, Wellington, FL (US)

(73) Assignee: Molekule Group, Inc., Palm Beach Gardens, FL (US)

( * ) Notice: Subject to any disclaimer, the term of this patent is extended or adjusted under 35 U.S.C. 154(b) by 292 days.

(21) Appl. No.: 17/474,598

(22) Filed: Sep. 14, 2021

(65) Prior Publication Data

US 2022/0080065 A1    Mar. 17, 2022

Related U.S. Application Data

(60) Provisional application No. 63/078,082, filed on Sep. 14, 2020.

(51) Int. Cl.
*A61L 2/10* (2006.01)
*A61L 9/20* (2006.01)
*B01D 46/00* (2022.01)

(52) U.S. Cl.
CPC ............... *A61L 2/10* (2013.01); *A61L 9/20* (2013.01); *B01D 46/0028* (2013.01);
(Continued)

(58) Field of Classification Search
CPC .......... A61L 2/10; A61L 9/20; A61L 2202/11; A61L 2202/16; A61L 2202/17;
(Continued)

(56) References Cited

U.S. PATENT DOCUMENTS 5,225,167 A    7/1993 Wetzel
5,505,904 A    4/1996 Haidinger et al.
(Continued)

FOREIGN PATENT DOCUMENTS

CN    2865691 Y    2/2007
CN    101437342 A    5/2009
(Continued)

OTHER PUBLICATIONS

Intellectual Property India, First Examination Report issued in Indian Patent Application No. 202037007585, and English-language translation, dated Mar. 28, 2022 (7 pages).
(Continued)

*Primary Examiner* — Kiet T Nguyen
(74) *Attorney, Agent, or Firm* — THE MARBURY LAW GROUP, PLLC (57) ABSTRACT

A robotic surface cleaning device is disclosed. The robotic surface cleaning device may be configured to traverse over a floor surface in a room area to disinfect various surface as well as disinfect the air in the room. The robotic surface cleaning device may include a maneuvering base. The robotic surface cleaning device may also include a support tower coupled to the maneuvering base and at least one deployable structure attached to the support tower, wherein the at least one deployable structure is capable of extending and retracting to pass over surfaces in the room area. The at least one deployable structure may include one or more ultraviolet (UV) light source configured to disinfect the surfaces in the room area. The support tower may include at least one air inflow vent configured to draw in room air, at least one air sanitizing unit configured with at least one array of UV light emitting diodes (LEDs), and at least one discharge vent configured to emit sanitized air.

7 Claims, 4 Drawing Sheets

(52) U.S. Cl.
CPC ....... *B01D 46/0039* (2013.01); *A61L 2202/11* (2013.01); *A61L 2202/16* (2013.01); *A61L 2202/17* (2013.01); *A61L 2209/12* (2013.01); *A61L 2209/14* (2013.01); *B01D 2273/30* (2013.01); *B01D 2279/55* (2013.01)

(58) Field of Classification Search
CPC ............. A61L 2209/12; A61L 2209/14; B01D 46/0028; B01D 46/0039; B01D 2273/30; B01D 2279/55
USPC .................................................... 250/455.11
See application file for complete search history.

(56) References Cited

U.S. PATENT DOCUMENTS

| | | | |
|---|---|---|---|
| 5,626,820 | A | 5/1997 | Kinkead et al. |
| 5,689,364 | A | 11/1997 | McGregor et al. |
| 5,761,908 | A | 6/1998 | Oas et al. |
| 5,964,792 | A | 10/1999 | Augustine |
| 6,039,926 | A | 3/2000 | Goldman |
| 6,053,968 | A | 4/2000 | Miller |
| 6,254,337 | B1 | 7/2001 | Arnold |
| 6,322,614 | B1 | 11/2001 | Tillmans |
| 6,464,760 | B1 | 10/2002 | Sham et al. |
| 6,541,777 | B1 | 4/2003 | Lombardo et al. |
| 6,797,044 | B2 | 9/2004 | Ou Yang et al. |
| 6,893,610 | B1 | 5/2005 | Barnes |
| 6,949,223 | B2 | 9/2005 | McEllen |
| 7,175,814 | B2 | 2/2007 | Dionisio |
| 7,303,612 | B2 | 12/2007 | Morrow et al. |
| 7,498,004 | B2 | 3/2009 | Saccomanno |
| 8,236,236 | B2 | 8/2012 | Garner |
| 8,980,178 | B2 | 3/2015 | Gaska et al. |
| 11,819,582 | B2 * | 11/2023 | Saxena ..................... A61L 2/24 |
| 2002/0144601 | A1 | 10/2002 | Palestro et al. |
| 2003/0170151 | A1 | 9/2003 | Hunter et al. |
| 2005/0000365 | A1 | 1/2005 | Nelsen et al. |
| 2005/0078473 | A1 | 4/2005 | Zuloff |
| 2005/0163646 | A1 | 7/2005 | Liang |
| 2005/0163648 | A1 | 7/2005 | Liang |
| 2005/0173352 | A1 | 8/2005 | Burrows et al. |
| 2005/0242013 | A1 | 11/2005 | Hunter et al. |
| 2006/0159594 | A1 | 7/2006 | Parker et al. |
| 2007/0102280 | A1 | 5/2007 | Hunter et al. |
| 2007/0196235 | A1 | 8/2007 | Shur et al. |
| 2008/0095661 | A1 | 4/2008 | Kohler |
| 2009/0004047 | A1 | 1/2009 | Hunter et al. |
| 2009/0041632 | A1 | 2/2009 | Day et al. |
| 2009/0084734 | A1 | 4/2009 | Yencho |
| 2009/0098014 | A1 | 4/2009 | Longstaff |
| 2009/0252646 | A1 | 10/2009 | Holden et al. |
| 2010/0132715 | A1 | 6/2010 | Litz |
| 2010/0143205 | A1 | 6/2010 | Engelhard |
| 2010/0260644 | A1 | 10/2010 | Day et al. |
| 2010/0279595 | A1 | 11/2010 | Hortsman et al. |
| 2011/0033346 | A1 | 2/2011 | Bohlen et al. |
| 2012/0118150 | A1 | 5/2012 | Brizes et al. |
| 2012/0168641 | A1 | 7/2012 | Lizotte |
| 2012/0273340 | A1 | 11/2012 | Felix |
| 2012/0285459 | A1 | 11/2012 | Sata et al. |
| 2013/0238042 | A1 | 9/2013 | Gildersleeve et al. |
| 2013/0313104 | A1 | 11/2013 | Yates et al. |
| 2014/0017135 | A1 | 1/2014 | Boodaghians et al. |
| 2014/0030144 | A1 | 1/2014 | Krosney et al. |
| 2014/0271374 | A1 | 9/2014 | Giles et al. |
| 2014/0348701 | A1 | 11/2014 | Kirschman |
| 2016/0038624 | A1 | 2/2016 | Krosney |
| 2017/0000916 | A1 | 1/2017 | Stibich et al. |
| 2017/0296690 | A1 | 10/2017 | Matsui et al. |
| 2017/0307234 | A1 | 10/2017 | Matschke et al. |
| 2019/0084852 | A1 | 3/2019 | Harris |
| 2019/0160190 | A1 | 5/2019 | Kreitenberg |
| 2020/0085983 | A1 * | 3/2020 | Ramanand ................ A61L 2/28 |
| 2020/0108166 | A1 | 4/2020 | Rhoden |
| 2020/0230267 | A1 | 7/2020 | Greenfield |
| 2020/0254133 | A1 | 8/2020 | Carr |
| 2021/0298391 | A1 | 9/2021 | Keene et al. |
| 2021/0299868 | A1 * | 9/2021 | Vitzrabin .................. A61L 2/24 |

FOREIGN PATENT DOCUMENTS

| | | |
|---|---|---|
| CN | 101639267 A | 2/2010 |
| CN | 202198889 U | 4/2012 |
| CN | 203980947 | 12/2014 |
| CN | 205181843 | 4/2016 |
| CN | 111093822 | 5/2020 |
| DE | 199 43 876 A1 | 3/2001 |
| EP | 2554583 A1 | 2/2013 |
| EP | 2921183 A1 | 9/2015 |
| JP | H6-12773 U | 2/1994 |
| JP | 11-014130 A | 1/1999 |
| JP | 2000-008178 A | 1/2000 |
| JP | 2000-070928 A | 3/2000 |
| JP | 2001-224672 A | 8/2001 |
| JP | 2001-293072 A | 10/2001 |
| JP | 2001520552 A | 10/2001 |
| JP | 2003-088571 A | 3/2003 |
| JP | 2004504869 A | 2/2004 |
| JP | 2005-166180 A | 6/2005 |
| JP | 2005-203437 A | 7/2005 |
| JP | 2005-253799 A | 9/2005 |
| JP | 2007-511279 A | 5/2007 |
| JP | 2008-259809 A | 10/2008 |
| JP | 2009-22903 A | 2/2009 |
| JP | 2009-181914 A | 8/2009 |
| JP | 2009-532200 A | 9/2009 |
| JP | 2011-530542 A | 12/2011 |
| JP | 2012-512723 A | 6/2012 |
| JP | 2012533720 A | 12/2012 |
| JP | 5432286 B2 | 12/2013 |
| JP | 2016530918 A | 10/2016 |
| KR | 20000017005 A | 3/2000 |
| KR | 200315033 | 5/2003 |
| KR | 200 397 497 Y1 | 10/2005 |
| KR | 100 894 823 B1 | 5/2009 |
| KR | 2012 0074746 A | 7/2012 |
| KR | 2020190000715 A | 3/2019 |
| WO | 98/47545 A2 | 10/1998 |
| WO | 02/04036 A1 | 1/2002 |
| WO | 2005/011753 A1 | 2/2005 |
| WO | 2007113537 A1 | 10/2007 |
| WO | 2010071814 A1 | 6/2010 |
| WO | 2011087100 A1 | 7/2011 |
| WO | 2015131243 A1 | 9/2015 |
| WO | 2016081703 A1 | 5/2016 |
| WO | 2017070359 A1 | 4/2017 |
| WO | 2020151918 A1 | 7/2020 |

OTHER PUBLICATIONS

Saudi Patent Office, Final Decision rejection with partial English-language translation received in corresponding Saudi Patent Application No. 518391412 issued Sep. 16, 2022.
Notification Concerning Transmittal of International Preliminary Report on Patentability received in corresponding Application No. PCT/US21/33752 dated Sep. 7, 2022.
Japanese Patent Office, Notice of Reasons for Refusal received in corresponding Japanese Patent Application No. 2018-540690 dated Aug. 30, 2022.
Korean Intellectual Property Office, "International Search Report and Written Opinion," issued in related International Application No. PCT/US2021/055670, dated Jul. 15, 2022 (9 pages).
Japanese Patent Office, Decision of Refusal issued in related Japanese Patent Application No. 2020-534160 dated Jan. 27, 2022.
International Preliminary Report on Patentability and Written Opinion for International Application No. PCT/US2021/055670, mailed May 11, 2023, 6 pages.
Substantive Examination Report received for Saudi Arabia Patent Application No. 520411446, dated May 21, 2023, 14 pages.

(56) References Cited

OTHER PUBLICATIONS

Saudi Authority for Intellectual Property, 1st Examination Report for PCT National Phase Application No. 518391412 and English-language translation dated Sep. 22, 2021(10 pages).
Saudi Authority for Intellectual Property, 2nd Examination Report for PCT National Phase Application No. 518391412 and English-language translation dated Feb. 16, 2022 (20 pages).
Notice of Preliminary Rejection received from the Korean Patent Office for related Application No. 10-2018-7014409 dated Jul. 25, 2023.
Extended European Search Report from the European Patent Office in related Application No. 14829593.4-1370 / 3024503 in International Application No. PCT/US2014/048144 dated Feb. 2, 2017.
International Search Report and Written Opinion of the International Searching Authority in International Application No. PCT/US2016/057932 dated Feb. 3, 2017.
International Preliminary Report on Patentability received from the Korean Intellectual Property Office in related International Application No. PCT/US2018/024229 mailed Dec. 19, 2019.
First Examination Report (FER) received from the Indian Patent Office in related Indian Patent Application No. 201637004406 dated Oct. 25, 2020.
International Preliminary Report on Patentability received from the Korean Intellectual Property Office in related International Application No. PCT/US2016/057932 dated Feb. 1, 2018.
International Preliminary Report on Patentability and Written Opinion of the International Searching Authority in related International Application No. PCT/US2018/024229 mailed Jul. 13, 2018.
International Search Report and the Written Opinion of the International Searching Authority received in related Application No. PCT/US2018/024229 dated Jul. 13, 2018.
Extended European Search Report received from the Hague Patent Office in related European Application No. EP 16 85 8222 dated May 22, 2019.
European Communication Pursuant to Rules 70(2) and 70a(2) EPC from the European Patent Office in related European Application No. EP 16 85 8222 dated Jun. 7, 2019.
First Notification of Reasons for Refusal received from the Japanese Patent Office in related Japanese Patent Application No. in JP 2018-540690 dated Sep. 3, 2020.
Written Opinion of the International Preliminary Examination Authority received in related Application No. PCT/US2018/024229 dated Oct. 24, 2019.
1st Office Action received from the European Patent Office in related European Patent Application No. 14 829 593.4-1104 dated Nov. 6, 2020.
International Search Report and the Written Opinion of the International Searching Authority received from the Korean Intellectual Property Office in related International Application No. PCT/US2018/024228 dated Jul. 13, 2018.
International Preliminary Report on Patentability received from the Korean Intellectual Property Office in related International Application No. PCT/US2018/024228 dated Dec. 16, 2019.
Extended European Search Report received in related European Patent Application No. 18851780.9-1104 / 3675919 PCT/US2018/024228 dated May 27, 2021.
Decision of Refusal received in related Japanese Patent Application No. 2018-540690 dated Jul. 1, 2021.
International Preliminary Report on Patentability and Written Opinion of the International Searching Authority in related International Application No. PCT/US2021/033752 mailed Sep. 16, 2021.
Japanese Patent Office, Reconsideration Report by Examiner before Appeal, issued in Japanese Patent Application No. 2018-540690, dated May 9, 2022, including English-language translation (4 pages).
Notice of Preliminary Rejection received from the Korean Patent Office in related Patent Application No. 10-2020-7008612 dated Feb. 1, 2023.
First Examination Report received for Saudi Arabia Patent Application No. 520411446, dated Dec. 28, 2022, 12 pages.
Office Action of Korean Patent Application No. 10-2020-7008612, mailed Feb. 1, 2023, 13 pages.
Trial and Appeal Decision for Japanese Patent Application No. 2018-540690, mailed Jan. 26, 2023, 4 pages.
Korean Intellectual Property Office, International Search Report and Written Opinion in corresponding International Application No. PCT/US2021/050342 mailed Dec. 31, 2021 (10 pages).
Japan Patent Office, Notice of Reasons for Refusal in Japanese Patent Application No. JP 2020-534160, Including English-language translation, dated Jan. 3, 2022, (7 pages).
Notice of Final Action received from the Korean Intellectual Property Office in related patent application No. KR 10-2018-7014409 dated Feb. 20, 2024.
First Examination Report in Indian Patent Application No. 201837013736, dated Aug. 25, 2020, 11 pages.
First Examination Report received for Saudi Arabia Patent Application No. 516370810, dated Nov. 13, 2017, 7 pages.
First Notification of Reasons for Refusal received for Japanese Patent Application No. 2016-530064 dated May 31, 2018, 15 pages.
Extended European Search Report in EP21867840.7, mailed Sep. 5, 2024, 6 pages.
Supplementary European Search Report from the Munich Patent Office received in related EP 21 96 1576 dated Oct. 7, 2024.

\* cited by examiner

INTEGRATED AIR SANITIZER AND SURFACE DISINFECTOR

RELATED APPLICATIONS

This application claims benefit of priority of U.S. Provisional Application Ser. No. 63/078,082 entitled "Integrated Air Sanitizer and Surface Disinfector", filed on Sep. 14, 2020, the entire content of which is incorporated herein by reference for all purposes.

BACKGROUND

There is a growing demand for improvements in indoor air quality in private and public settings to reduce the transmission of pathogens. As information about the health risks related to exposure to various types of contaminants becomes available, interest in maintaining a healthy indoor environment has expanded to include residential and commercial settings. In particular, the presence of certain molds, bacteria, and/or viruses has been shown to cause long-lasting and far-reaching health problems. Consequently, prevention and treatment of indoor contaminants is of interest across industries as well as individuals.

SUMMARY OF THE INVENTION

Systems, methods, and devices of various embodiments enable a robotic surface cleaning device to travel over a floor surface in room area. In some embodiment systems, methods, and devices, the robotic surface cleaning device may include a maneuvering base, a support tower coupled to the maneuvering base, and at least one deployable structure attached to the support tower. In some embodiment systems, methods, and devices, the support tower may include at least one air inflow vent configured to drawn in room air, at least one air sanitizing unit configured with at least one array of ultraviolet (UV) light emitting diodes (LEDs), and at least one discharge vent configured to emit sanitized air. In some embodiment systems, methods, and devices, the at least one deployable structure may be capable of extending and retracting to pass over surfaces in the room area. In some embodiment systems, methods, and devices, the at least one deployable structure may include one or UV light source configured to disinfect the surfaces in the room area.

In some embodiment systems, methods, and devices, the at least one air sanitizing unit may include at least one high-efficiency particulate air (HEPA) filter, at least one fan and motor assembly configured to generate an airflow, and at least one sterilizing chamber. In some embodiment systems, methods, and devices, the at least one sterilizing chamber may include an inner surface at least partially lined with an ultraviolet (UV) reflective material. In some embodiment systems, methods, and devices, the at least one array of UV LEDs may be mounted on the inner surface. In some embodiment systems, methods, and devices, the at least one array of UV LEDs may be configured to irradiate the airflow.

In some embodiment systems, methods, and devices, the robotic surface cleaning device may also include at least one power supply. In some embodiment systems, methods, and devices, the at least one array of UV LEDs may be configured to emit radiation at one or more wavelength within a range of 240-280 nm. In some embodiment systems, methods, and devices, the at least one array of UV LEDs is configured to irradiate the airflow with a UV radiation dosage sufficient to reduce airborne pathogens.

In some embodiment systems, methods, and devices, the robotic surface cleaning device may further include at least one drive motor and at least one wheel coupled to the maneuvering base.

In some embodiment systems, methods, and devices, the robotic surface cleaning device may further incorporate at least one sterilizing unit. In some embodiment systems, methods, and devices, the at least one sterilizing unit may include a portion of a duct at least partially lined with an ultraviolet (UV) reflective material, a plurality of hollow structures positioned within the portion of the duct, each comprising an external UV reflective surface, and at least one array of UV light emitting diodes (LEDs) mounted on a surface of at least one of the plurality of hollow structures. In some embodiment systems, methods, and devices, the sterilizing unit may be configured to replace a section of an existing duct in the HVAC system such that airflow within the HVAC system passes through the sterilizing unit before exiting from one or more vent.

In some embodiment systems, methods, and devices, the at least one sterilizing unit may also include a power supply housed within at least one of the hollow structures. In some embodiment systems, methods, and devices, each of the at least one array of UV LEDs may be connected to a printed circuit board assembly (PCBA) within the hollow structure on which the array is mounted. In some embodiment systems, methods, and devices, the at least one hollow structure on which the at least one array of UV LEDs is mounted may be positioned at an end of the sterilizing unit upstream from an airflow exit point. In some embodiment systems, methods, and devices, the at least one array of UV LEDs may be configured to emit radiation at one or more wavelength within a range of 240-280 nm. In some embodiment systems, methods, and devices, the UV LEDs may be configured to irradiate the air within the HVAC system with a UV radiation dosage sufficient to reduce airborne pathogens.

In some embodiment systems, methods, and devices, the robotic surface cleaning device may further include at least one drive motor and at least one wheel coupled to the maneuvering base. In some embodiment systems, methods, and devices, the robotic surface cleaning device, the at least one deployable structure may be capable of rotating such that the one or more UV light source is positioned to irradiate in an upward direction. In some embodiment systems, methods, and devices, the at least one air sanitizing unit may be configured to be operated independently from the at least one deployable structure.

BRIEF DESCRIPTION OF THE DRAWINGS

These and other features, aspects, and advantages of the present invention will become better understood with regard to the following description, appended claims, and accompanying drawings where:

DETAILED DESCRIPTION OF THE DRAWINGS

In the description and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "UV radiation" is used herein to mean high energy UV-C photons with wavelengths shorter than 290 nm, which are capable of traversing cellular walls. In various embodiments, the UV radiation utilized for air treatment may be at one or multiple wavelengths within the range of 200 to 320 nm range.

The terms "flux" and "radiation flux" are used herein to mean the amount of radiation at the specified wavelength that reaches the surface of airborne pathogens. The terms "dwell time" and "residence time" are used herein to refer to the duration of time that the airborne pathogens remain exposed to the radiation flux.

The terms "contaminants" is used herein to refer to impurities, including all of biological agents (e.g., pathogens), chemical agents, pollutant particles, volatile organic compounds, and chemical vapors.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1 The term "at most" followed by a number is used herein to denote the end of a range ending with that number (which may be a range having 1 or 0 as its lower limit, or a range having no lower limit, depending upon the variable being defined). When, in this specification, a range is given as "(a first number) to (a second number)" or "(a first number)–(a second number)," this means a range whose lower limit is the first number and whose upper limit is the second number.

While the specification concludes with claims defining the features of embodiments of the invention that are regarded as novel, it is believed that the invention will be better understood from a consideration of the following description in conjunction with the figures, in which like reference numerals are carried forward.

Currently implemented approaches to reducing pathogens involve decontamination of room surfaces between occupancies. This can be accomplished by irradiating the room and all of its surfaces with high-level ultra-violet (UV) radiation or by spraying the room with hydrogen peroxide mist. However, the room must be unoccupied and isolated and if anyone wishes to enter the room during this process, significant protective equipment must be worn.

Surface disinfecting robotic surface cleaning device s have been developed that irradiate high touch areas in offices, on airplanes and in hospitals. However, the high doses of UV radiation employed may be outside of safe limits for human exposure, requiring operation at night. Such robotic surface cleaning device s may utilize am ultraviolet (UV) vacuum tube or xenon pulse discharge tube as the UV light source, which may be mounted to the body or to articulating structures.

These surface cleaning devices are evolving capabilities but they have essentially no capability to remove pathogens from the air. This is a serious limitation to the surface cleaner's overall effectiveness. Aerosols and dust particles laden with pathogens are suspended in the air. Large, heavy particles settle first and progressively finer particles settle more slowly on the freshly sterilized surfaces. The surfaces are cleanest right after exposure and gradually become more infected late at night even before occupants have arrived.

Radiation sources, such as UV lamps, have been used in portable air purification devices and HVAC systems to inhibit growth of bacteria and certain molds on condensing coils and/or drain pans. Filtering devices such as activated carbon filters, high energy particulate air (HEPA) filters, and electrostatic filters have been used to remove particulate matter and pollutants from indoor air.

The various embodiments provide a robotic surface cleaning device that includes an air sanitizing unit. In various embodiments, the air sanitizing unit may be sufficiently compact so as to not increase the size of the robotic surface cleaning device. In this manner, the surface cleaning device is able to navigate narrow cleaning paths throughout a room.

An air intake area may be located near the base of the surface cleaning device, with the component of the air sanitizing unit located within the structural spine that supports the articulating arms. An air discharge area may be located near the top of the structural spine.

In various embodiments, the air sanitizing unit may have an airflow of around 200 cubic feet per minute, single pass pathogen kill capability and HEPA particulate removal. The volume of action for the robotic surface cleaning device may be assuming 12 feet×12 feet×8 feet around the robot as it performs its surface cleaning process. Therefore, the air exchange rate of air achieved by the sanitizing unit of the device may be at least 9 air change per hour (ACH). The combined capability of providing clean air and clean surfaces provides an improved level of room air sanitization.

In various embodiments, the air sanitizing unit may include one or more sterilizing chamber that contains at least one array of light emitting diodes (LEDs) for treating an airflow circulating within a room in order to significantly reduce the number of contaminants therein. For example, at least one sterilizing chamber may include one or more array of UV LEDs capable of directing ultraviolet radiation toward the air stream, thereby sterilizing microbes and halting reproduction.

In an embodiment, one or more sensor may be used to monitor air quality characteristics and/or equipment status. Air quality characteristics monitored may include, but are not limited to, airflow, temperature, humidity, and contaminant levels. Equipment parameters monitored may include, but are not limited to, UV LED performance. If an irregularity is noted, a monitoring system may automatically provide a notification to an indicator external to the HVAC system.

The sterilizing unit according to various embodiments may be installed into an existing HVAC system to eradicate pathogens in the output air of the HVAC system. The sterilizing unit may be located at the end of a ventilation duct where the air flows into a specific room or larger area. The sterilizing unit may be tailored to different sizes depending on the robotic surface cleaning device.

The electronics for the components of the air sanitizing unit (e.g., for the LEDs, fan, and motor) may be enclosed within the base of the robotic surface cleaning device. bodies of the units, and only require only one low wattage AC line to supply power.

Figure 1:
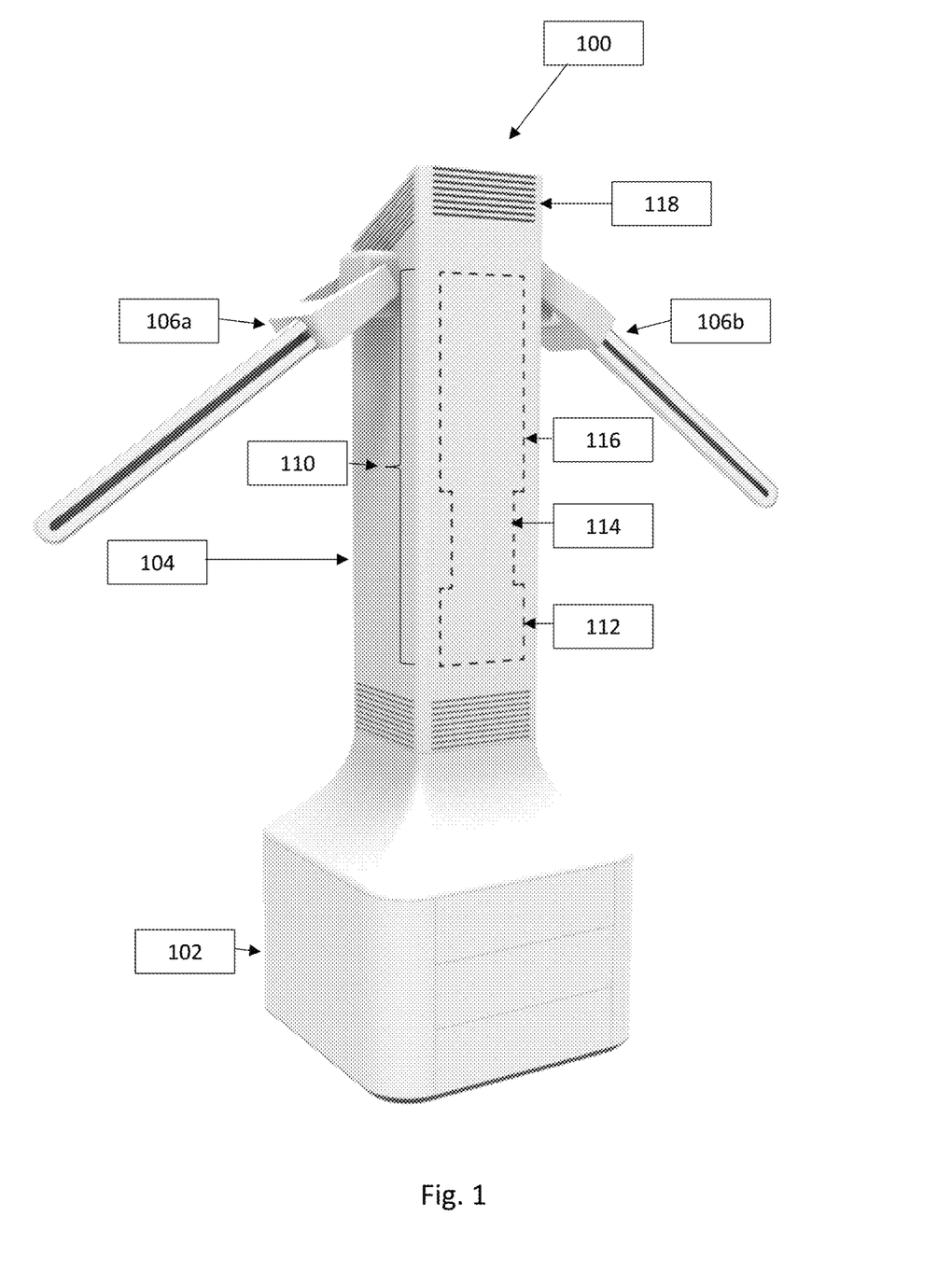
FIG. 1 shows a representative diagram of a robotic surface cleaning device according various embodiments.

FIG. 1 illustrates an example robotic surface cleaning device 100 according to various embodiments. The cleaning device 100 may include a maneuvering robotic base 102, a support tower 104, and at least two deployable arms 106a, 106b with UV light sources. In various embodiments, the deployable arms 106a, 106b may be around 6 feet in length when extended, and may be configured to disinfect surfaces at a high output. The UV light sources on the arms 106a, 106b may be vacuum tube UV lamps. In various embodiments, the deployable arms 106a, 106b may be compactly folded to facilitate mobility for the cleaning device as it navigates its cleaning route through a room area. The extended span of the deployable arms 106a, 106b may serve to enhance the various exposure angles and viewing paths for the UV radiation, reducing the amount of contaminated surface that remain untreated. In some embodiments, the at least two deployable arms 106a, 106b may be able to rotate such that the UV light sources are positioned to irradiate upward. Such upward irradiation may provide the ability, for example, to disinfect various bottom surfaces (e.g., tables) or surfaces above the cleaning device 100.

The support tower 104 may include various components for air treatment within the room. Specifically, room air may enter an air inflow vent 108 positioned near the base 102 and be passed through an air sanitizing unit 110 housed within the body of the support tower 104. The air sanitizing unit 110 may include, in various embodiments, at least one HEPA filter 112, a fan/motor component 114, and a sterilizing chamber 116. Cleaned air (i.e., airflow that has passed through the air sanitizing unit 110) may exit the device through a discharge vent 118. In this manner, contaminated aerosols and dust particles laden with pathogens that may be suspended in the air may be removed from the air. Thus, such particles may be prevented from re-contaminating disinfected surfaces.

The sterilizing chamber 116 may be lined with a UV reflective coating, and may include at least one UV LED may be mounted on the inner surface. The number of UV LEDs in each array, and the number and location of the arrays, may be customized based on the size of the sterilizing chamber 116 and the robotic surface cleaning device 100. The UV LED arrays may be connected to one or more printed circuit board assembly (PCBA) within the air sanitizing unit, which may be powered by a power supply housed within the support tower 104 or the maneuvering base 102. In various embodiments, the power supply may include various sub-components and features as would be necessary to provide and regulate power to the various components In various embodiments, the sterilizing chamber 116 may include at least one UV sensor positioned at the top, close to the discharge vent 118. In some embodiments, the UV sensor may be coupled to a UV function display (not shown) that may be positioned on the outside of the robotic surface cleaning device 100 in order to provide feedback to a user and ensure normal operation without requiring disassembly of the device.

In various embodiments, the area of airflow within the support tower 104 between the sterilizing chamber 116 and the discharge vent 118 may be coated with a UV absorbent material. The UV absorbent material may be, for example, a layer that includes titanium dioxide and/or zinc oxide. In some embodiments, the discharge vent 118 may also be covered with a UV absorbent screen also made of any of a variety of UV absorbent materials. Such UV absorbent material may prevent the unwanted escape of any UV radiation originating from the sterilizing chamber 116.

The robotic surface cleaning device according to various embodiments may include a computer or microprocessor including at least one memory storing firmware and software for controlling movement of the device and operation of the deployable arms. In some embodiments, the computer or microprocessor may be programmed to automatically shut off the UV illumination sources on the arms and/or to deactivate the robotic surface cleaning device 100 when a prescribed dose of UV has been delivered. In other embodiments, the computer or microprocessor may be programmed to automatically shut off the UV illumination sources on the arms and/or to deactivate the robotic surface cleaning device 100 when the presence of an animate object (e.g., person, animal, etc.) may be detected.

In various embodiments, the robotic surface cleaning device 100 may include at least one battery that supplies operating power to the computer and/or to the UV illumination sources (e.g., UV lamps on the deployable arms, PCBAs/UV LEDs of the sterilizing chamber, etc.), as well as other components, such as the at least one drive motor. In various embodiments, the robotic surface cleaning device 100 may include a DC/AC converter.

The robotic surface cleaning device 100 may also include at least one drive motor each coupled to a wheel on the bottom of the maneuvering robotic base. In some embodiments, the at least one drive motor may be controlled by signals from the computer or microprocessor, which may provide steering for the robotic surface cleaning device.

Navigation in the room to avoid obstacles may be achieved using any of a variety of sensors, including, but not limited to, ultrasonic distance sensors, proximity sensors, infrared beam/photoelectric sensors, global positioning system (GPS) sensors, etc., which may be incorporated in a multi-sensor platform. In some embodiments, the robotic surface cleaning device may employ vision simultaneous localization and mapping (VSLAM) to intelligently track the space in the room to be cleaned. Specifically, using VSLAM, the cleaning device may dynamically build a map of a room while tracking its own position using one or more camera. In some embodiments, the robotic surface cleaning device may employ GPS tracking or technology to map a room and track its position. Alternatively, a wire or guide may be laid on the floor and used to direct the cleaning device along a particular track and/or to prevent the device from running "out of bounds" into furniture or other fixtures in the room. In various embodiments, the robotic surface cleaning device may include at least one wireless transceiver enabling connection to a remote location and/or to mobile devices.

Figure 2:
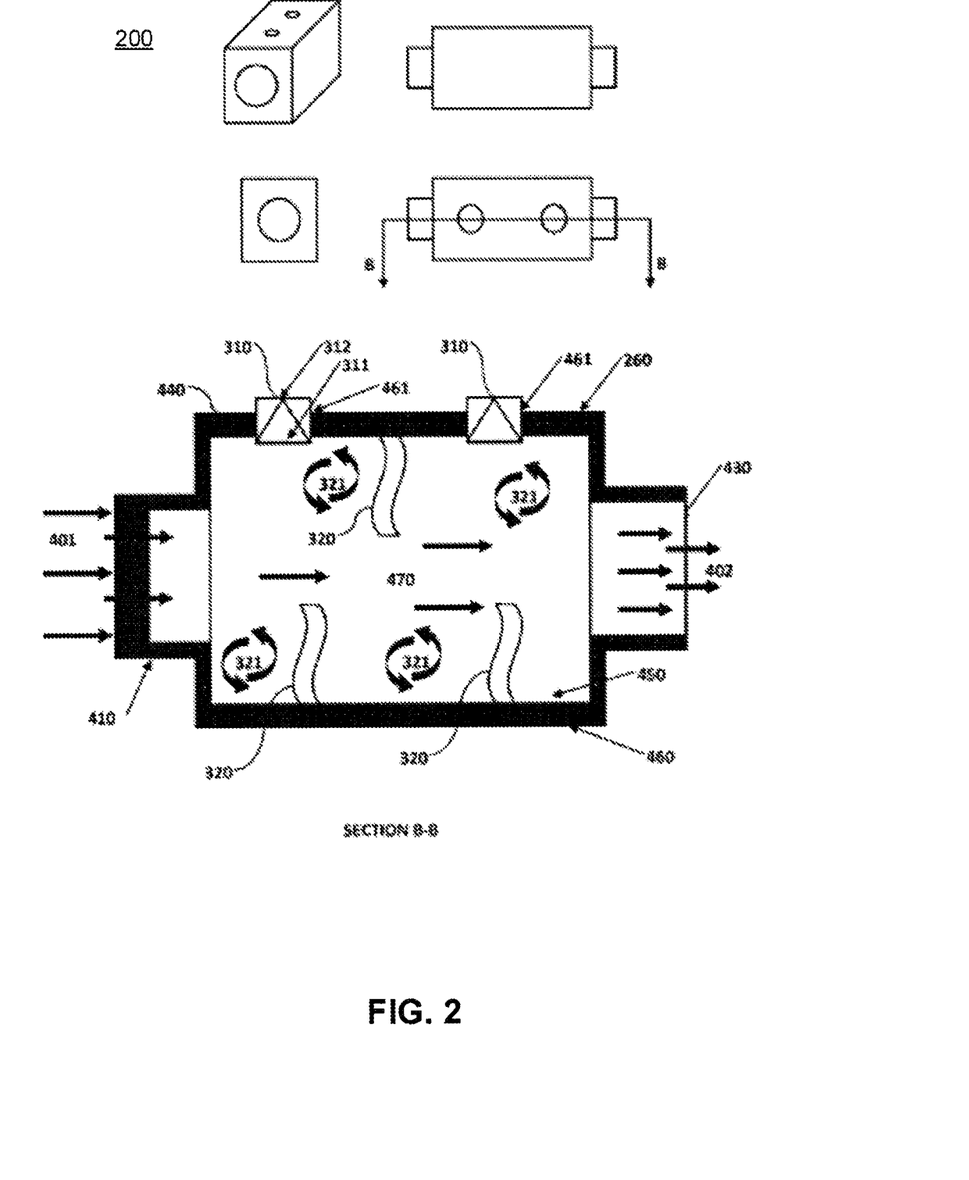
FIG. 2 shows a composite view of an embodiment of the invention, including perspective, orthographic projection, and cross-sectional views of a system for sterilizing and disinfecting air that is suitable to be installed within a robotic surface cleaning device according to various embodiments.

FIG. 2 is a diagram illustrating components of an example system 200 for sterilizing and disinfecting air that is suitable to be installed within a robotic surface cleaning device according to various embodiments. With reference to FIGS. 1-2, the system 200 may represent one or more portion of the robotic surface cleaning device 100 (e.g., air sanitizing unit 110, including the sterilizing chamber 116).

In various embodiments, the system 200 may include an inlet portion configured to receive an air flow 401, a high efficiency filter 410 (e.g., a HEPA filter) operatively coupled to the inlet portion 410, an outlet portion 430 configured to expel the sterilized air flow 402, and a sterilizing chamber 260. The sterilizing chamber 260 may include a non-UV light transmissive surface portion 440 made of a UV light reflective inner surface 450, and an outer surface 460, the non-UV light transmissive surface portion 440 defining a substantially enclosed area 470 between the inlet portion 410 and the outlet portion 430 through which the air flow passes. The UV light reflective inner surface 450 may be formed by a coating of a highly reflective material, such as polished aluminum.

In some embodiments, the sterilizing chamber 260 may include one or more turbulators 320 positioned with the airflow in the substantially closed area 470 to create turbulence 321 within the airflow. The sterilizing chamber 260 may also include one or more aperture, and one or more UV light emitting diode (LED) 310 inserted into the one or more aperture 461 such that a UV radiation is emitted into the substantially enclosed area 470 thereby exposing said air flow to said UV radiation.

Embodiments of the sterilizing chamber 260 may comprise an inner surface treatment that provides for a diffuse reflection of the UV radiation. The use of diffuse reflectors may increase the efficiency of the UV irradiation field by scattering the UV light rays, as opposed to specular reflective surfaces (such as polished metals) that reflect the UV ray at an angle equal to the angle at which the ray hits the surface. In some embodiments, a diffuse UV reflective surface may be accomplished through a micro-texture, a coating, or a laminated material, such as polytetrafluoroethylene (PTFE).

In some embodiments, the sterilizing chamber 116 and other components of the air sanitizing unit may be secured within the support structure of the cleaning device by one or more fastener. The number and shape of the various components (e.g., sterilizing chamber, UV LED array, fan/motor, HEPA filter, etc.) may depend on and vary according to the dimensions of the robotic surface cleaning device. In some embodiment, the sterilizing chamber may be cylindrical or approximately cylindrical, or may have the shape of a rectangular prism.

The number of UV LEDs in each array, and the positions in which they are mounted, may be customized based on the size of the sterilizing chamber. In some embodiments, the UV LED arrays may be positioned near the bottom of the air sanitizing chamber, closest to the fan/motor and farthest from the discharge vent. In various embodiments, the power source (e.g., one or more battery) providing operating power to the UV LEDs and/or corresponding PCBA(s) may include various sub-components and features as would be necessary to provide and regulate power to the various components.

In various embodiments, the air sanitizing chamber may be variously shaped to satisfy treatment and design needs. For example, components including the sterilizing chamber may be positioned such that the incoming air stream achieves optimum exposure to the UV radiation via the UV reflective material on the interior surface (e.g. substantially enclosed area 470).

The robotic surface cleaning device 100 in various embodiments may be used for surface and airflow cleaning in residences, commercial buildings, hospitals, public spaces, and other environments where it is desired to deliver clean, pure airflow and to sterilize surfaces without requiring an empty space.

In various embodiments, the power supply for providing power to the PCBA(s), UV LEDs, UV light sources on the deployable arms 106a, 106b, the drive motor(s), the computer or microprocessor, and any other components of the cleaning device may include a regulation means. Such power supply may be, but is not limited to, a power plug, a voltage regulator, a transformer, a circuit breaker, and/or other circuitry for powering, monitoring, and regulating the UV LEDs through one or more PCBA, as well as powering, monitoring, and regulating the movement of the deployable arms and the UV light sources for surface cleaning. In some embodiments, the power supply may be a rechargeable battery pack, which may be charged by conventional charging means.

In various embodiments, an interlock switch may be incorporated into the cleaning device that serves to shut off the UV LEDs in the sterilizing chamber if any part of support tower were to become open. In this manner, a user may be protected from exposure to the UV radiation. The interlock switch may include various components known in the art including, but not limited to, relays, contact closures, and circuit breakers.

As will be clear to those of ordinary skill of the art, as well as within the scope and of this disclosure, that while the above embodiments have been described as a UV sanitization unit apparatus installed in a robotic surface cleaning device, it may equivalently be installed in other devices and/or systems Further, various embodiments may comprise one or more than one of any component.

An embodiment of the sterilizing chamber 116 may comprise a cross-sectional area that is substantially consistent throughout the length, while a further embodiment may comprise a cross-sectional area that varies in shape and/or size throughout the length of the sterilizing chamber. The cross section of the sterilizing chamber 116 may be circular, elliptical, rectangular, or any other shape as may be chosen to optimize the path of the airflow through the air sanitizing unit. In some embodiments, the sterilizing unit may be designed to sustain a specific volumetric throughput and to fit within the support tower of the particular robotic surface cleaning device.

The sterilizing chamber 116 itself may be manufactured utilizing various methods and materials as may be known in the art including, but not limited to, extruded plastics, formed metals, or a combination of materials.

The UV LEDs in various embodiments may be selected based upon the desired wavelength and power rating, as well as size and expected lifespan. The number and distribution of these UV LEDs in arrays within a sterilizing chamber 116 may be such as to maximize the radiant flux within the sterilizing chamber, while preventing substantial UV radiation escape from the discharge vent 118.

The various electrical components, such as the PCBAs for the UV LEDs, the interlock switch, the UV sensor, and the UV function display, may be electrically connected to and powered by the power supply. The power supply may further comprise one or more of an electronics and control module, processing means, and power regulation means.

Embodiments of the present invention may comprise a device for supplying clean air to one or more room while simultaneously cleaning surfaces of the one or more room. Embodiments of the device may comprise: at least one sterilizing chamber including a plurality of UV LEDs capable of achieving at least a baseline kill rate of airborne pathogens.

In some embodiments, the UV LEDs in the at least one array emit radiation at one or more wavelength within the range of 240-280 nm, such as within the range of 260-270 nm.

The internal surface of one or more section of the sterilizing chamber 116 may be coated with a reflective material.

In various embodiments, the configuration of at least one sterilizing chamber 116 within the support tower 104 may be designed to manage the UV radiation flux and effectively sanitize the airflow without compromising the desired airflow rate. Generally, increasing the length of the pathway may lead to longer residence time for the airflow, and therefore providing space for more center bodies configured with UV LED arrays to increase effectiveness of the UV radiation in killing airborne pathogens. However, since such increases lengthen the path of the airflow also increases the pressure drop over the system, the sterilizing unit may be designed with a length to mitigate such pressure drop. Also, while a high level of reflectance within the sterilizing unit generally maximizes the effectiveness of the UV LEDs, the sterilizing unit may be designed and positioned to prevent reflected radiation from escaping the discharge vent. In various embodiments, optimal positioning of the at least one array of UV LEDs may be obtained using UV radiation ray tracing technology.

In some embodiments, the airflow of the air sanitizing unit may be within the range of about 100 cubic feet per minute (cfm) to about 700 cfm.

An electronics and control module may be incorporated to regulate power supplied to various components in embodiment cleaning devices. In some embodiments, an electronics and control module may be implemented as a computer or microprocessor. The electronics and control module may be provided as one or multiple units/integrated circuits, and may be coupled to the power supply for one of more sterilizing chamber, UV sensor, UV function display, and/or interlock switch.

Figure 3:
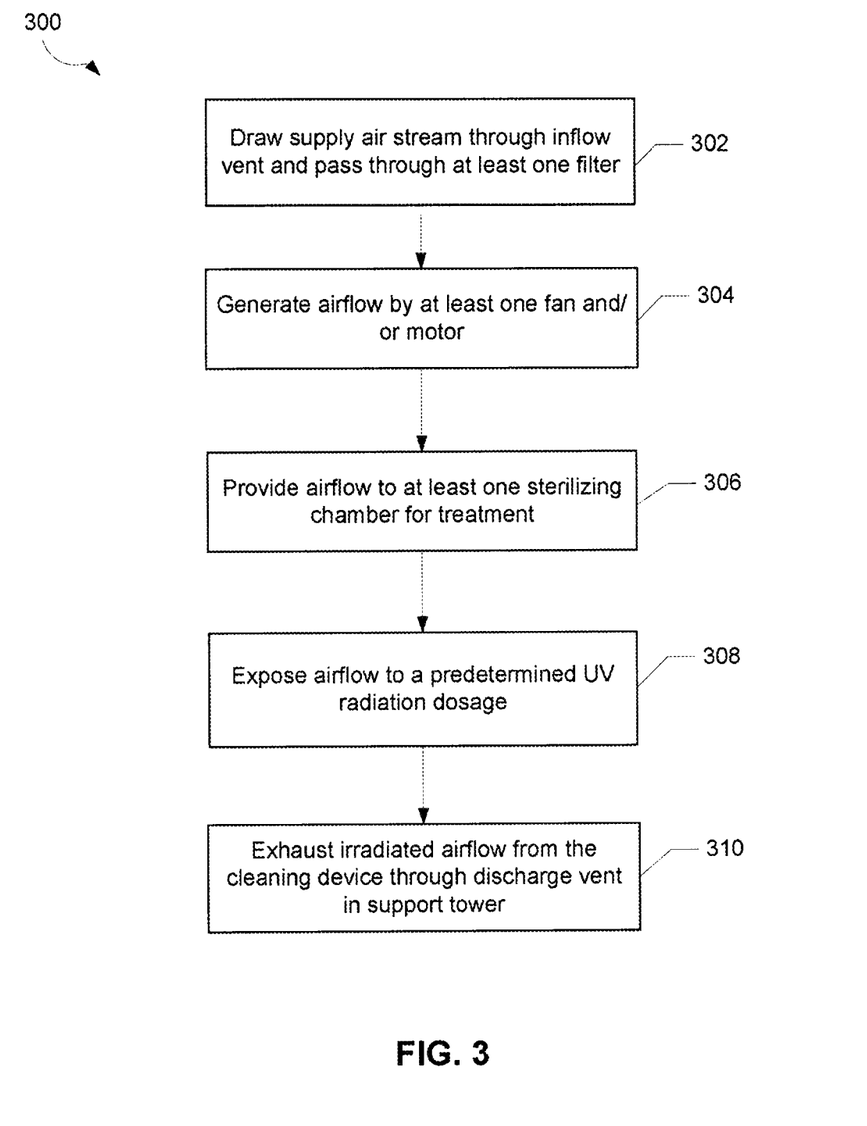
FIG. 3 is a process flow diagram illustrating a method for reducing airborne pathogens contaminants in an airflow of a room with a robotic surfaced cleaning device according to various embodiments.

FIG. 3 shows an embodiment method 300 for purifying air within a building or room that is able to be cleaned by a robotic surface cleaning device (e.g., system 100 of FIG. 1). In various embodiments, purifying the air according to method 300 may be performed simultaneously with surface disinfection within the building or room, or may be performed without surface disinfection (e.g., during occupancy). In this manner, the air purification may be performed by a mobile unit.

Referring to FIGS. 1-3, in block 302, a supply air stream may be drawn into the air sanitizing unit through an inflow vent (e.g., 108) and passed through at least one filter that removes fine particulates (e.g., HEPA filter) and/or that adsorbs harmful gasses (e.g., volatile organic chemical filter). In block 304, an airflow may be generated by at least one fan and/or motor (e.g., 114). In block 306, the airflow may be provided to at least one sterilizing chamber (e.g., 116, 260) within the support tower of the cleaning device for treatment.

In block 308, the airflow may be exposed to a predetermined UV radiation dosage by passing through the substantially enclosed area of the one or more sterilizing chamber (e.g., 116, 260). The predetermined UV radiation dosage may be achieved by optimizing the number and position of UV LED arrays and the materials used, and configuring the sterilizing chamber to allow for a necessary residence time. In various embodiments, the predetermined UV radiation dosage may be sufficient to kill or disable at least 90% of airborne pathogens within the airflow.

In block 310, the irradiated airflow may be exhausted from the cleaning device through a discharge vent (e.g., 118) near the top of the support tower (e.g., 104). In some embodiments, the inner surface of the support tower 104 between the outlet portion (e.g., 430) of the sterilizing chamber and the discharge vent may be lined with UV absorbing material.

In some embodiments, additional air treatment functionality may be added to a robotic surface cleaning device by including specialized components. For example, a UV sensor (e.g., 214) may be disposed within the in or connected to a sterilizing chamber 116 of embodiment robotic surface cleaning devices 100 in order to monitor the radiation flux and ensure proper operation. In various embodiments, such UV sensor may use one or more UV photodetector, such as those based on gallium nitride (GaN), indium gallium nitride (InGaN), and/or aluminum gallium nitride (AlGaN) materials. In various embodiments, the UV sensor may be configured to communicate with an externally visible indicator (e.g., UV function display 220) to confirm to the user that the device is working. In some embodiments, the indicator may be in in wireless communication with one or more UV sensor connected to the one or more sterilizing chamber.

Figure 4:
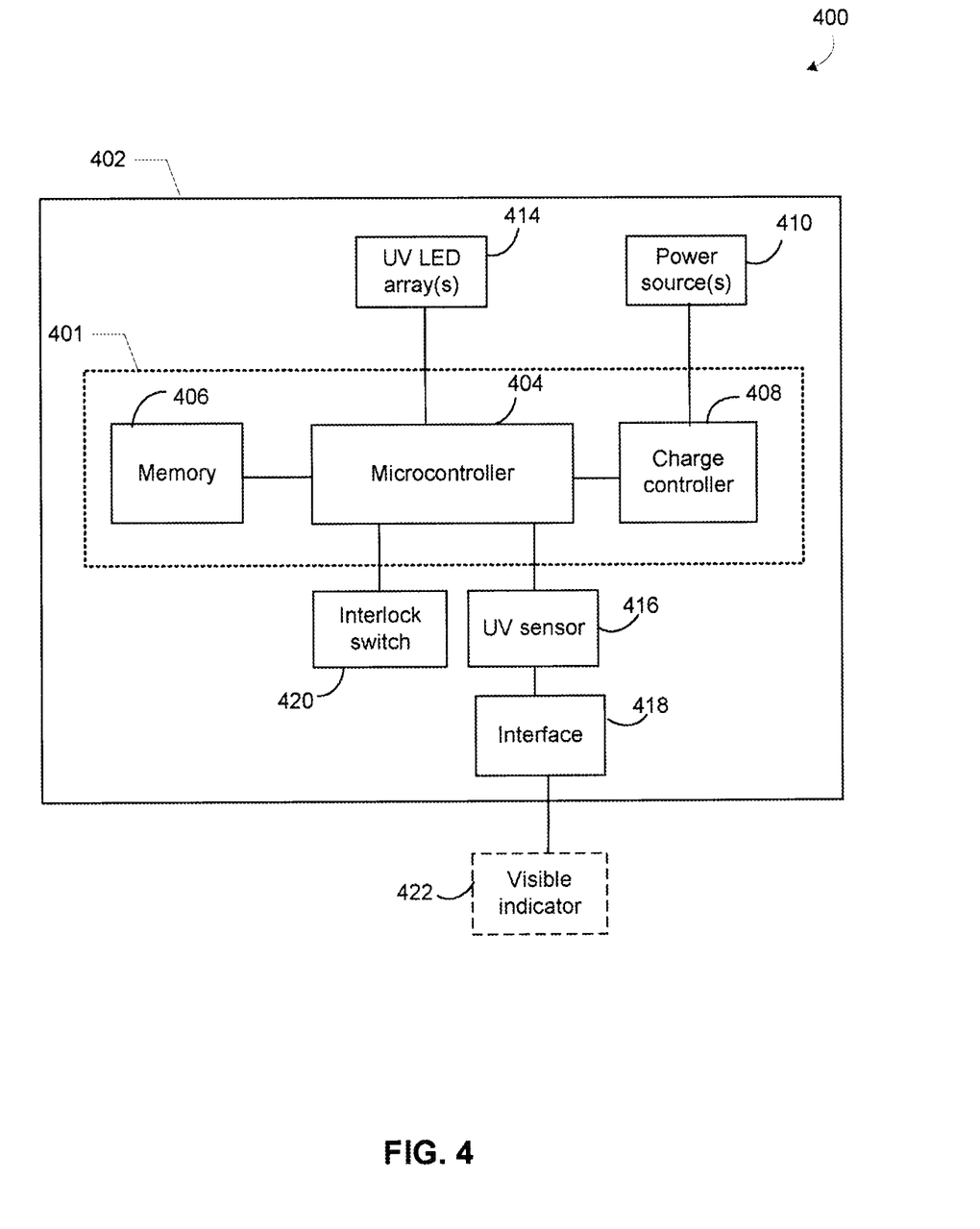
FIG. 4 is a component block diagram of a robotic surface cleaning device including an air sanitizing unit according to various embodiments.

FIG. 4 illustrates air treatment components of an example robotic surface cleaning device 400. In device 400, at least one electronics and control module 401 may be implemented on a circuit board (e.g., PCBA(s)). With reference to FIGS. 1-4, the circuit board may be positioned either within or outside an air sanitizing unit (e.g., 110), and may be separate from one or more controller for the other components of the robotic surface cleaning device.

The electronics and control module 402 may include a microcontroller 404 coupled to a memory device 406 and a charge controller 408. The charge controller 808 may connect to at least one power source 410, which may be an AC power supply and/or a battery. Other air treatment components within the cleaning device 400 may include one or more UV LED array 414, a UV sensor 416, and an interlock switch 420. The interlock switch 420 may be coupled to the microcontroller 404. The UV sensor 416 may be connected to an interface 418 that connects one or more visible indicator 422. The visible indicator 422 may be provided as an external component, which may be part of another device or system (e.g., a smartphone, tablet, etc.). The interface 418 may connect the visible indicator 822 through a wireless communication link.

The UV LEDs of the one or more array may be electrically connected to the electronics and control module and fixedly attached to mated openings in the walls of a portion of the sterilizing chamber such that the UV LEDs irradiate inside the sterilizing chamber. The UV sensor may be electrically connected to the electronics and control module and fixedly attached to a mated opening in the wall of the sterilizing chamber such that the sensor can detect irradiance levels.

In light of the foregoing description, it should be recognized that embodiments in accordance with the present invention can be realized in numerous configurations contemplated to be within the scope and spirit of the claims. Additionally, the description above is intended by way of example only and is not intended to limit the present invention in any way, except as set forth in the following claims.

What is claimed is:

1. A robotic surface cleaning device configured to traverse over a floor surface in a room area, comprising:
 a maneuvering base;
 at least one drive motor and at least one wheel coupled to the maneuvering base;
 a support tower coupled to the maneuvering base; and
 at least one deployable structure attached to the support tower, wherein the at least one deployable structure is capable of extending and retracting to pass over surfaces in the room area, and wherein the at least one deployable structure comprises one or more ultraviolet (UV) light source configured to clean the surfaces in the room area;
 wherein the support tower comprises:
  at least one air inflow vent configured to draw in room air;
  at least one air sanitizing unit configured with at least one array of UV light emitting diodes (LEDs); and
  at least one discharge vent configured to emit sanitized air;
 wherein the robotic surface cleaning device is configured to navigate in the room area using at least one sensor.

2. The robotic surface cleaning device of claim 1, wherein the at least one sanitizing unit comprises:
 at least one high-efficiency particulate air (HEPA) filter;
 at least one fan and motor assembly configured to generate an airflow; and
 at least one sterilizing chamber comprising an inner surface at least partially lined with an ultraviolet (UV) reflective material,
 wherein the at least one array of UV LEDs is mounted on the inner surface, and wherein the at least one array of UV LEDs is configured to irradiate the airflow.

3. The robotic surface cleaning device of claim 1, further comprising at least one power supply.

4. The robotic surface cleaning device of claim 1, wherein the at least one array of UV LEDs is configured to emit radiation at one or more wavelength within a range of 240-280 nm.

5. The robotic surface cleaning device of claim 1, wherein the at least one array of UV LEDs is configured to irradiate the room air with a UV radiation dosage sufficient to reduce airborne pathogens.

6. The robotic surface cleaning device of claim 1, wherein the at least one deployable structure is capable of rotating such that the one or more UV light source is positioned to irradiate in an upward direction.

7. The robotic surface cleaning device of claim 1, wherein the at least one air sanitizing unit is configured to be operated independently from the at least one deployable structure.

* * * * *